(12) United States Patent
Wendel-Mitoraj (10) Patent No.: US 11,523,763 B2
(45) Date of Patent: Dec. 13, 2022

(54) IMPLANTABLE ELECTRODE DEVICE AND A METHOD FOR MANUFACTURING THEREOF

(71) Applicant: BrainCare Oy, Tampere (FI)

(72) Inventor: Katrina Wendel-Mitoraj, Pirkkala (FI)

(73) Assignee: BRAINCARE OY, Tampere (FI)

(*) Notice: Subject to any disclaimer, the term of this patent is extended or adjusted under 35 U.S.C. 154(b) by 333 days.

(21) Appl. No.: 15/525,843

(22) PCT Filed: Nov. 2, 2015

(86) PCT No.: PCT/EP2015/075479
§ 371 (c)(1),
(2) Date: May 10, 2017

(87) PCT Pub. No.: WO2016/074974
PCT Pub. Date: May 19, 2016

(65) Prior Publication Data
US 2017/0319092 A1     Nov. 9, 2017

(30) Foreign Application Priority Data
Nov. 11, 2014   (DE) .......................... 102014116477.6

(51) Int. Cl.
*A61B 5/05*     (2021.01)
*A61B 5/291*    (2021.01)
*A61N 1/05*     (2006.01)

(52) U.S. Cl.
CPC ................ *A61B 5/291* (2021.01); *A61N 1/05* (2013.01); *A61B 2562/028* (2013.01); *A61B 2562/125* (2013.01); *H01L 2924/0002* (2013.01)

(58) Field of Classification Search
CPC .. A61N 1/0534; A61N 1/0529; A61N 1/0543; A61N 1/0539; A61N 1/36046;
(Continued)

(56) References Cited

U.S. PATENT DOCUMENTS 6,624,510 B1    9/2003   Chan et al.
8,209,023 B2 *  6/2012   Zhou ..................... A61N 1/0543
                                                                607/115
(Continued)

FOREIGN PATENT DOCUMENTS

CN    102387746 A    3/2012
CN    103446665 A    12/2013
(Continued)

OTHER PUBLICATIONS

Hsu et al. "Effect of Thermal and Deposition Processes on Surface Morphology, Crystallinity, and Adhesion of Parylene-C". Sensors and Materials, vol. 20, No. 2 (2008) 087-102. (Year: 2008).*
(Continued)

*Primary Examiner* — Joseph A Stoklosa
*Assistant Examiner* — Brian M Antiskay
(74) *Attorney, Agent, or Firm* — Cuenot, Forsythe & Kim, L.L.C.

(57) ABSTRACT

An implantable electrode device includes a carrier made of a polymer material, at least one measurement electrode formed by an electrically conducting pad located on the carrier, wherein the electrically conducting pad has a contact surface, a barrier layer enclosing the carrier by covering all surfaces of the carrier, wherein the contact surface of the electrically conducting pad is exposed to an outside environment, at least one electrically conducting trace, and at least one electrically conducting terminal. The electrically conducting trace can electrically connect the measurement electrode to the electrically conducting terminal. A surface of the implantable electrode device on a side on which the measurement electrode is located can have a maximum valley depth or a maximum peak height between the contact surface of the measurement electrode and a meanline of a surface of the implantable electrode device, excluding mea- (Continued)

surement electrodes, being equal to or smaller than 100 micrometres.

19 Claims, 5 Drawing Sheets

(58) Field of Classification Search
CPC .. A61N 1/0531; A61N 1/0553; A61N 1/3756;
A61N 1/0476; A61N 1/0492; A61N 1/04;
A61N 1/0551; A61N 1/0556; A61B
5/0476; A61B 5/04001; A61B 5/4094;
A61B 5/0422; A61B 5/0006; A61B
5/6814; A61B 5/04012; A61B 5/6868;
A61B 5/4064; A61B 5/24; A61B
2562/125; A61B 2562/164; A61B 5/6833;
A61B 5/287
USPC ............... 600/372–373, 378, 393, 544–545;
607/115–118
See application file for complete search history.

(56) References Cited

U.S. PATENT DOCUMENTS

| | | | | |
|---|---|---|---|---|
| 8,214,032 | B2* | 7/2012 | Mech | A61K 9/0009 427/2.1 |
| 8,666,505 | B2* | 3/2014 | O'Brien | A61B 5/03 607/115 |
| 9,592,377 | B2* | 3/2017 | Greenberg | A61N 1/36082 |
| 2006/0173263 | A1* | 8/2006 | He | A61B 5/04001 600/378 |
| 2006/0225274 | A1 | 10/2006 | Greenberg et al. | |
| 2007/0123963 | A1* | 5/2007 | Krulevitch | A61N 1/05 607/115 |
| 2009/0221896 | A1 | 9/2009 | Rickert et al. | |
| 2009/0264972 | A1 | 10/2009 | Zhou et al. | |
| 2010/0023102 | A1 | 1/2010 | Spruit | |
| 2010/0145176 | A1* | 6/2010 | Himes | A61B 5/4064 600/378 |
| 2010/0200538 | A1 | 8/2010 | Petisce et al. | |
| 2011/0237921 | A1 | 9/2011 | Askin, III et al. | |
| 2012/0112347 | A1 | 5/2012 | Eckhardt et al. | |
| 2012/0172960 | A1* | 7/2012 | Gabriel | A61N 1/0551 607/116 |
| 2013/0144365 | A1* | 6/2013 | Kipke | A61B 5/0478 607/93 |
| 2014/0262462 | A1 | 9/2014 | Shah et al. | |
| 2015/0335258 | A1* | 11/2015 | Masmanidis | A61B 5/6868 600/378 |
| 2016/0066789 | A1* | 3/2016 | Rogers | A61N 1/05 604/20 |

FOREIGN PATENT DOCUMENTS

| | | |
|---|---|---|
| DE | 102006008501 B3 | 10/2007 |
| JP | 2009544438 A1 | 12/2009 |
| JP | 2012517597 A | 8/2012 |
| KR | 20140075905 A | 6/2014 |

OTHER PUBLICATIONS

WIPO Int'l. Appln. No. PCT/EP2015/075479, International Search Report, dated Feb. 15, 2016, 5 pg.
WIPO Int'l. Appln. No. PCT/EP2015/075479, dated May 19, 2016, 8 pg.
WIPO Appln. PCT/EP2015/075479, International Preliminary Report on Patentability, dated May 16, 2017, 9 pg.
JP Appln. No. 2017-524470, Office Action (with English translation), dated Oct. 1, 2019, 10 pg.
CN Appln. No. 201580061052.2, Office Action (with English translation), dated Aug. 16, 2019, 17 pg.
Von Metzen et al., The effects of annealing on mechanical, chemical, and physical properties and structural stability of Parylene C, Biomed Microdevices, Springer Science+Business Media New York, pp. 727-735 (Mar. 15, 2013), accessed from https://pubmed.ncbi.nlm.nih.gov/23494595/.
Völker et al., Influence of annealing on microstructure and mechanical properties of ultrafine-grained Ti45Nb, Materials and Design 179, ScienceDirect, pp. 1-11 (May 16, 2019) (hereinafter "Volker"), accessed from https://www.sciencedirect.com/science/article/pii/S0264127519303028.

* cited by examiner

IMPLANTABLE ELECTRODE DEVICE AND A METHOD FOR MANUFACTURING THEREOF

CROSS-REFERENCE TO RELATED APPLICATIONS

This application claims the benefit of International Application No. PCT/EP2015/075479 filed on Nov. 2, 2015, which claims the benefit of Germany Application Number 10 2014 116 477.6 filed on Nov. 11, 2014. Patent Applications PCT/EP2015/075479 and 10 2014 116 477.6 are fully incorporated herein by reference.

BACKGROUND

The present invention relates to an implantable electrode device.

Neurological disorders like epilepsy are affecting millions of people worldwide. Costs spent on prevention, early diagnosis and treatment of neurological disorders, in particular brain disorders contribute to a significant amount of the total health care costs.

A major technical obstacle regarding research and innovation in the areas of prevention, early diagnostics and treatment of brain diseases such as epilepsy is based on the fact that reliable, long-term, and continuous monitoring still relies on a manually-maintained seizure diary kept by the patient. These diaries tend to be incomplete due to a variety of reasons.

SUMMARY

An implantable electrode device includes a carrier made of a polymer material, wherein the carrier is flexible and electrically isolating, at least one measurement electrode formed by an electrically conducting pad located on the carrier, wherein the electrically conducting pad has a contact surface, a barrier layer enclosing the carrier by covering all surfaces of the carrier, wherein the contact surface of the electrically conducting pad is exposed to an outside environment, at least one electrically conducting trace, and at least one electrically conducting terminal. The electrically conducting trace can electrically connect the measurement electrode to the electrically conducting terminal. A surface of the implantable electrode device on a side on which the measurement electrode is located can have a maximum valley depth or a maximum peak height between the contact surface of the measurement electrode and a meanline of a surface of the implantable electrode device, excluding measurement electrodes, being equal to or smaller than 100 micrometres.

A system can include a data processor and an implantable electrode device. The implantable electrode device can include a carrier made of a polymer material, wherein the carrier is flexible and electrically isolating, at least one measurement electrode formed by an electrically conducting pad located on the carrier, wherein the electrically conducting pad has a contact surface, a barrier layer enclosing the carrier by covering all surfaces of the carrier, wherein the contact surface of the electrically conducting pad is exposed to an outside environment, at least one electrically conducting trace, and at least one electrically conducting terminal. The electrically conducting trace can electrically connect the measurement electrode to the electrically conducting terminal. A surface of the implantable electrode device on a side on which the measurement electrode is located can have a maximum valley depth or a maximum peak height between the contact surface of the measurement electrode and a meanline of a surface of the implantable electrode device, excluding measurement electrodes, being equal to or smaller than 100 micrometres.

A method for manufacturing an implantable electrode device can include providing a substrate, applying a liquid polymer material onto the substrate, confining the liquid polymer material to define a desired height, curing the liquid polymer material to form a solid, flexible and electrically isolating polymer material providing a carrier, depositing an electrically conducting material on the carrier, structuring of the electrically conducting material in order to define at least one measurement electrode formed by an electrically conducting pad having a contact surface, at least one electrically conducting trace, and at least one electrically conducting terminal, wherein the electrically conducting trace electrically connects the measurement electrode and the terminal, removing the substrate, and coating of a barrier layer onto the structure comprising the carrier and the electrically conducting material so that the barrier layer encloses the structure by covering all surfaces of the structure. A surface of the implantable electrode device on a side on which the measurement electrode is located can have a maximum valley depth or a maximum peak height between the contact surface of the measurement electrode and a meanline of the surface of the implantable electrode device excluding the at least one measurement electrode being equal to or smaller than 100 micrometres.

BRIEF DESCRIPTION OF THE DRAWINGS

FIGS. 2 a) and b) depict schematic top and bottom views of an alternative embodiment of an electrode device according to the present invention.

FIGS. 4 a) to i) depict a sequence of schematic cross-sectional views of yet another embodiment of an electrode device according to the present invention during manufacturing thereof.

DETAILED DESCRIPTION

The present invention relates to an implantable electrode device comprising a carrier made of a polymer material, wherein the carrier is flexible and electrically isolating, at least one measurement electrode formed by an electrically conducting pad located on the carrier, wherein the electrically conducting pad has a contact surface, at least one electrically conducting trace, and at least one electrically conducting terminal, wherein the trace electrically connects the measurement electrode and the terminal.

The present invention also relates to a method for manufacturing such an implantable electrode device.

Furthermore, the present invention relates to a method for implanting such an implantable electrode device.

One would like to have patients under long-term and continuous monitoring of an electroencephalography (EEG) device. It is possible to equip a patient with electrodes on the outer surface, i.e. skin of his head and collect the data on a long-term basis in a portable data recorder. However, this turns out to be a severe limitation of the patient's quality of life with respect to esthetic aspects and wearing comfort.

It is an object of the present invention to provide an electrode device being implantable to a patient's body, in particular under the patient's skin in his head, which can stay implanted over a long time in order to provide reliable, long-term and continuous monitoring of the patient's brain activities.

At least one of the above objects is solved by an implantable electrode comprising a carrier made of a polymer material, wherein the carrier is flexible and electrically isolating, at least one measurement electrode formed by an electrically conducting pad located on the carrier, wherein the electrically conducting pad has a contact surface, at least one electrically conducting trace, and at least one electrically conducting terminal, wherein the trace electrically connects the measurement electrode and the terminal, wherein the implantable electrode device further comprises a barrier layer enclosing the carrier by covering all surfaces thereof, including a front side, a back side and side faces of the carrier, wherein the contact surface of the conducting pad is exposed to an outside environment, and wherein a surface of the electrode device on a side on which the measurement electrode is located has a maximum valley depth or a maximum peak height between the contact surface of the measurement electrode and a meanline of the surface of the electrode device excluding the at least one measurement electrode being equal to or smaller than 60 micrometres or wherein a surface of the electrode device on a side on which the measurement electrode is located has a maximum valley depth or a maximum peak height between the contact surface of the measurement electrode and a meanline of the surface of the electrode device excluding the at least one measurement electrode being larger than 60 micrometres and wherein the maximum linear extension of the contact surface is equal to or less than 100 micrometres.

In order to be implantable an electrode device must have a carrier being flexible to adopt the shape of a patient's part of the body, e.g. his cranium. Furthermore, the actual measurement electrodes formed of an electrically conducting material must be supported by the carrier material requiring the carrier also to be electrically isolating in particular in cases, wherein a plurality of measurement electrodes is located on a single carrier.

At the same time, mechanically stable mounting of the electrically conducting material of the measurement electrode on the carrier must be provided even under conditions, wherein the carrier is bent when implanting or withdrawing it from a patient's body.

Last but not least, an electrode device in order to be implantable must fulfill certain requirements regarding patient safety. One of these requirements is that the device must be safe from falling apart in the patient's body in order to guarantee that no parts or substances remain in the body when withdrawing the device. Furthermore, all materials used must be biologically safe, e.g. non-toxic.

An electrode device used as a long-term implant must be stable over a long period of time and be retractable even after having been implanted for a long time without the electrode device breaking into parts when pulling it out of the patient's body.

Typical carrier materials which can be used in an embodiment when designing an implantable electrode device are for example silicon-based organic polymers, preferably polydimethylsiloxane (PDMS). An alternative material for the carrier is for example polyimide. These materials have a sufficient flexibility and are electrically isolating.

However, a disadvantage of materials available for the carrier is that they typically have rather low bonding forces between their surface and other materials applied thereon. These bonding forces are further reduced once the surface of the carrier is wetted with water or any other liquid. This is a particular problem for an implantable electrode device, which will stay in a liquid containing environment at a patient's body over a long period of time.

Thus according to the present invention the implantable electrode device comprises a barrier layer enclosing the carrier on all surfaces thereof avoiding that any liquid enters along the interface between a surface of the carrier and any other material bonded to the surface of the carrier.

Thus the barrier layer forms an encapsulation for the structure comprising the carrier and the electrically conducting material wherein only the contact surface of the measurement electrode and once applicable a contact surface of the terminal are exposed to an outside environment.

It is an important property of the barrier layer encapsulating the carrier that the barrier layer is electrically isolating and impermeable for liquids.

A material bonded to the surface of the carrier in an embodiment is the electrically conducting material forming the measurement electrode, the electrically conducting trace and the electrically conducting terminal.

However, in an embodiment a material bonded onto the surface of the carrier can also be the barrier layer itself. Alternatively, in an embodiment a material bonded on the surface of the carrier can be any intermediate layer.

In an embodiment of the present invention, the electrically conducting material forming the measurement electrode and/or the electrically conducting trace and/or the electrically conducting terminal is provided by metal. In an embodiment the metal used in order to form the electrically conducting material is one of a group consisting of platinum, gold, chromium, titanium, iridium, tungsten, a platinum/iridium alloy, and stainless steel or a combination thereof. Alternatively, other conducting materials such as carbon nano tubes (CNT) could be used.

In an embodiment, the contact surface of the measurement electrode has a quadrangular shape, a polygonal shape, a circular shape or an elliptical shape.

In an embodiment of the present invention the electrically conducting material forming the electrically conducting pad and/or the electrically conducting trace and/or the electrically conducting terminal have a thickness in a range of 100 nanometers to 250 nanometers, and preferably has a thickness of 200 nanometers.

While in this description embodiments have been described with respect to the detailed designs of one measurement electrode, one terminal, and one trace connecting the measurement electrode and the terminal, there are preferred embodiments, wherein a plurality of measurement electrodes, traces and terminals are provided at the electrode device.

In an embodiment of the present invention, a surface of the barrier layer forms an outer surface of the electrode device on a side of the electrode device on which the measurement electrode is located. As it is a requirement of the implantable electrode device that the contact surface of the measurement electrode is exposed to an outside environment, the contact surface is not covered by the barrier layer. In a further embodiment a contact surface of the terminal is not covered by the barrier layer, but is exposed to an outside environment in order to electrically contact the terminal.

In an embodiment of the implantable electrode according to the present invention, the barrier layer is made of parylene. Parylene is the trade name for a variety of chemical vapor deposited poly (p-xylylene) polymers used as moisture and dielectric barriers. Parylene C is one example of a parylene. In an embodiment of the present invention, a halogenated hydrocarbon is used as a parylene.

Parylene has a low friction, is flexible and has a pin-hole free surface making it easy to remove an electrode device being coated with parylene. The surface properties of the parylene reduce encapsulation growth. Parylene furthermore is strong in the sense it can withstand high tensioning forces in order to withstand a removal process when the electrode device is retracted from a patient's body.

Parylene has a further advantageous as it is a barrier for most fluids and is electrically insulating. Furthermore, parylene is considered biocompatible.

Another characteristic of parylene is that it provides an adhesion promoting layer for the electrically conducting material, in particular for a metallization of e.g. platinum, while at the same time having a coefficient of thermal expansion which is between a metal, in particular platinum, and a polymer material used for the carrier, in particular PDMS.

In an embodiment of the present invention, the barrier layer covers a front side, a backside and the side surfaces of the carrier such that it forms a tight envelope surrounding and encapsulating the carrier. The expression that the barrier layer covers the surfaces of the carrier does not necessarily mean that the barrier is in direct contact with the surfaces of the barrier, but an intermediate layer or an undercoating may be arranged between the carrier and the barrier layer.

In an embodiment of the present invention, the electrically conducting material forming the terminal and/or the trace and/or the electrically conducting pad of the measurement electrode is formed on a coating applied to the carrier.

In a particular embodiment, this coating is provided by the identical material forming the barrier layer.

Thus in a particular embodiment, the coating is applied on the surface of a carrier, wherein the electrically conducting material of the conducting pad and/or the trace and/or terminal is formed on the coating and the barrier encloses the carrier, the coating as well as the electrically conducting material only leaving the contact surface exposed to an outside environment.

In a particular embodiment, an additional undercoating is provided between the surface of the carrier and the coating and/or between the coating and the barrier layer.

In a particular embodiment, the undercoating is made of silane. This is in particular applicable to embodiments, wherein the barrier layer and/or the coating are formed by parylene.

It is a major issue of the implantable electrode according to the present invention that it can be retracted from the patient's body by pulling it out through a tiny incision in the patient's skin by pulling the electrode device at one end thereof. This will only be possible under the following conditions, wherein most preferably both of them are fulfilled simultaneously:

The integrity of the implantable electrode device must be unaffected by its environment even after a long time of being implanted. This is well guaranteed by the barrier layer enclosing the carrier. Furthermore, the electrode device must have a mechanical stability which allows pulling of the device out of the patient's body.

The latter requirement can be fulfilled by two alternative approaches, i.e. by reducing encapsulation growth on the one hand and by making the electrode device more rigid on the other hand. While in an embodiment of the invention both aspects may be addressed simultaneously according to all embodiments the surface of the electrode device on sides on which the measurement electrode is located is designed, such that encapsulation growth is reduced.

In order to do so the surface of the electrode device on a side on which the measurement electrode is located has a maximum valley depth or a maximum peak height between the contact surface of the measurement electrode and a meanline of the surface of the electrode device excluding the at least one measurement electrode being equal to or smaller than 60 micrometers.

Surprisingly, it has been demonstrated that the smaller the maximum valley depth or maximum peak height between the contact surface and the meanline of the surface of the electrodes excluding the at least one measurement electrode is, the less encapsulation growth occurs. Furthermore, the smaller the maximum valley depth or the maximum peak height between the contact surface of the measurement electrode and the meanline of the surface of the electrode device excluding the measurement electrode is, the smaller the forces are, which hold the implantable electrode in place after encapsulation growth occurred. These forces applied by encapsulation growth counter act any forces applied on the implantable electrode device when pulling out the electrode device from the patient.

Alternatively, the surface of the electrode device decide on which the measurement electrode is located can be designed such that it has a maximum valley depth or a maximum peak height between the contact surface of the measurement electrode and a meanline of the surface of the electrode device excluding the at least one measurement electrode which is larger than 60 micrometers and wherein simultaneously the maximum linear extension of the contact surface is equal or less than 100 micrometers.

It has been found that, the smaller the maximum linear extension of the contact surface, the smaller are the forces which hold the electrode device in place after encapsulation growth occurred. The maximum linear extension of the contact surface is its diameter once the contact surface is of circular shape or it is the length of its longest side once the contact surface is quadrangular. In an embodiment, wherein the electrode has an elliptical shape, the maximum linear extension is the major axis (also denoted as the transverse diameter) of the ellipse.

In a particular embodiment, wherein the maximum valley depth or the maximum peak height between the contact surface of the measurement electrode and a meanline of the surface of the electrode device excluding the measurement electrode is larger than 60 micrometers the maximum linear extension of the contact surface is equal or less than 90 micrometers, preferably less than 80 micrometers and most preferred equal to or less than 70 micrometers.

According to the present application, the meanline of the surface of the electrode device is a straight line which by its mathematical definition intersects the actual profile of the surface of the electrode device such that the sum over all deviations of the meanline from the actual profile is minimized. It is apparent that the meanline is defined by the surface of the electrode device excluding the one or a plurality of measurement electrodes.

In a particular embodiment of the present invention the surface of the electrode device on a side on which the measurement electrode is located has a maximum valley depth or maximum peak height between the contact surface of the measurement electrode and a meanline of the surface of the electrode device excluding the at least one measurement electrode being equal to or smaller than 50 micrometers, preferably equal to or smaller than 30 micrometers.

In another embodiment of the present invention the surface of the electrode device on a side on which the measurement electrode is located has a maximum valley depth or a maximum peak height between the contact surface of the measurement electrode and a meanline of the surface of the electrode device excluding the at least one measurement electrode being equal to or larger than 5 micrometers, preferably equal to or larger than 10 micrometers, and most preferably equal to or larger than 12 micrometers.

In an embodiment of the present invention, the electrode device has a strip-like shape, being easy to insert and remove from the patient's body. In a particular embodiment, the long sides of an electrode device having an essentially quadrangular footprint are straight lines in order to enhance the possibility to retract the electrode device from a patient's body.

In an embodiment of the present invention, the electrode device has an elongated shape having a length in a range from 4 cm to 25 cm, preferably in a range from 10 cm to 20 cm. This way electrodes can be provided, which cover the entire hemisphere of a patient's cranium.

In order to avoid rupture of the electrode device when retracting it from a patient's body the carrier and the barrier layer in an embodiment have an ultimate tensile strength to withstand removal from the patient's body in one piece such that the actual value depends on the size and plurality of the electrodes present on the device.

Furthermore, in order to provide the required strength of the electrode device against rupture the electrode device has a thickness in a range from 200 micrometers to 2,500 micrometers, preferably in a range from 800 micrometers to 1,500 micrometers.

This overall thickness of the electrode device is contributed to by the thickness of the carrier, the thickness of the conducting material as well as the thickness of the barrier layer and once applicable any intermediate layer, like the coating.

In a particular embodiment, the carrier has a thickness in a range from 800 micrometers to 1,200 micrometers, in particular a thickness of 1,000 micrometers.

In a further embodiment, the barrier layer has a thickness in a range from 5 micrometers to 20 micrometers, preferably in a range from 8 micrometers to 15 micrometers and most preferably has a thickness of about 10 micrometers.

In another embodiment of the present invention, the coating applied between the carrier and the electrically conducting material has a thickness in a range from 5 micrometers to 10 micrometers, preferably has a thickness of about 7 micrometers.

The electrically conducting material, preferably a metal, in an embodiment of the present invention has a thickness in a range from 80 nanometers to 250 nanometers, and preferably has a thickness of 200 nanometers.

When choosing the thicknesses of the different layers or components of the implantable electrode according to an embodiment of the present invention these thicknesses are not chosen independently of each other.

One of the major boundary conditions when designing an implantable electrode device is that the electrode device must be flexible i.e. can be bent to have a curved shape to fit the patient's body. Simultaneously, the bonding of the electrically conducting material in particular a metallization to the underlying material, in particular either to the carrier or to the coating applied to the carrier must be stable. In an embodiment, this can be achieved once the electrically conducting material is in contact with the underlying material in a plane, wherein stress and strain under mechanical bending of the electrode device neutralizes each other. This plane is the so called mechanical neutral plane (also known as the neutral layer or neutral surface) wherein all stresses applied on one side of the electrically conducting material are compensated by the strains applied on the other side of the electrically conducting material.

The thickness $d_{below}$ of the material below the electrically conducting material and the thickness $d_{above}$ of the material above the electrically conducting material must fulfill the following simplified relation:

$$Y_{below} d_{below} = Y_{above} d_{above}$$

wherein $Y_{below}$ is the Young's modulus of the material below the electrically conducting material and $Y_{above}$ is the Young's modulus of the material above the electrically conducting material.

This simplified equation assumes that all the material applied on top of the metallization is a single type of material as is the material on which the electrically conducting material is applied. This in particular holds once the carrier is thick when compared to the coating or no coating is applied and the thickness of the barrier on the surface of the carrier opposite the metallization is also thin when compared to the thickness of the carrier.

The above relation further assumes that the electrically conducting material is thin enough such that its stiffness or Young's modulus does not contribute significantly to the mechanical properties of the implantable electrode device when considered as the whole structure.

In a further embodiment of the present invention, the implantable electrode device further comprises an interface equipment electrically coupled to the terminal. Such an interface equipment in an embodiment comprises a wireless communication device that wirelessly communicates measurement data acquired of the measurement electrode to a data processor located outside the patient's body. In particular, in an embodiment the interface equipment is implantable as is the rest of the implantable electrode device.

At least one of the above objects is also solved by a combination of a data processor and an implantable electrode device as it has been described before, wherein the data processor comprises an interface equipment in communication with the interface equipment of the implantable electrode device when in use.

This data processor can be a processing unit of an EEG device, which can process, evaluate and/or display the data collected by the implantable electrode device.

At least one of the above objects is also solved by a a method for manufacturing an implantable electrode device comprising the steps providing a substrate, applying a liquid polymer material onto the substrate, confining the liquid polymer material to define a desired height, curing the liquid polymer material to form a solid, flexible and electrically isolating polymer material providing a carrier, depositing an electrically conducting material on the carrier, structuring of the electrically conducting material in order to define at least one measurement electrode formed by an electrically conducting pad having a contact surface, at least one electrically conducting trace, and at least one electrically conducting terminal, wherein the trace electrically connects the measurement electrode and the terminal, removing the substrate, coating of a barrier layer onto the structure comprising the carrier and the electrically conducting material such the barrier layer encloses the structure by covering all surfaces thereof, wherein a surface of the electrode device on a side on which the measurement electrode is located has a maximum valley depth or a maximum peak height between the contact surface of the measurement electrode and a meanline of the surface of the electrode device excluding the at least one measurement electrode being equal to or smaller than 60 micrometres or wherein a surface of the electrode device on a side on which the measurement electrode is located has a maximum valley depth or a maximum peak height between the contact surface of the measurement electrode and a meanline of the surface of the electrode device excluding the at least one measurement electrode being larger than 60 micrometres and wherein the maximum linear extension of the contact surface is equal to or less than 100 micrometres, and opening the barrier layer above the contact surface of the measurement electrode such that the contact surface is exposed to an outside environment.

It is apparent that this method is used in order to process or manufacture an electrode device as it has been described in various embodiments above.

In as far as aspects of the implantable electrode device have been described above, they are also applicable for manufacturing the implantable electrode device as it is described here and vice versa.

The substrate, which is used in order to provide a surface for the processing of the implantable electrode device is a tool for the manufacturing process, but is not part of the completed and finalized electrode device. Thus, the substrate is removed before the final steps of processing are carried out, e.g. by etching or lapping.

In an embodiment of the present invention, the substrate comprises one of the following materials, a plastic material, e.g. PMMA, glass, a semiconductor material, e.g. silicon, or any combination thereof.

In an embodiment, the liquid polymer material is poured onto the substrate, then spacers are positioned on the substrate in order to define the height of the carrier. Then a second substrate is lowered onto the spacers such that the liquid polymer material assumes a thickness defined by the spacers. After curing a solid polymer material as a carrier is formed on the substrate.

In an embodiment, an undercoating is provided on top of the carrier in order to provide better adhesion of either an electrically conducting layer or the barrier layer or another coating on the carrier.

In a particular embodiment wherein the carrier is made of PDMS and the barrier layer is made of parylene the undercoating processed is silane.

In order to form an undercoating of silane in an embodiment the structure comprising the carrier and the electrically conducting material is first cleaned and then placed in a silane solution over a predetermined time. After removal of the structure from the silane solution the structure is air dried and then rinsed or cleaned again.

In an embodiment wherein the barrier layer is made of parylene, the barrier layer is applied by chemical vapor deposition.

In an embodiment, wherein the electrically conducting material is made of metal, the metal is sputtered or evaporated onto the carrier or onto a coating provided on the carrier.

Structuring of the electrically conducting material may for example be achieved by laser ablation. However, also conventional etching methods may be applied in order to structure the electrical conducting material.

The final barrier layer encloses the structure comprising the carrier and the electrically conducting material as a moisture barrier such that moisture cannot or can only hardly enter the device. However, at least the contact surface of the electrode at the final electrode device must be exposed to an outside environment. Thus the barrier layer above the contact surface of the measurement electrode in a further process step is opened, i.e. taken away. This opening may e.g. be achieved by laser ablation. In an embodiment of the present invention also the terminal of the electrically conducting material can be opened in a final step in order to enable contact of the terminal.

In another embodiment, a number of implantable electrode devices is manufactured on a single substrate, such that before applying the final barrier layer on all surfaces of each of the electrode devices, the different electrode devices have to be cut apart from each other.

The step of cutting the carrier, such that multiple electrode devices are separated can be carried out either before or after removal of the substrate.

Furthermore, one of the above objects is also solved by a method for implanting an implantable electrode device as it has been described above into a human or animal body, wherein the electrode device is inserted under the patient's skin, preferably between two skin layers.

In a particular embodiment, the electrode device is implanted at the patient's head between the skin and the cranium or between two layers of the skin.

Further advantages, features and applications of the present invention will become apparent from the following description of an embodiment and the figures attached.

Figure 1:
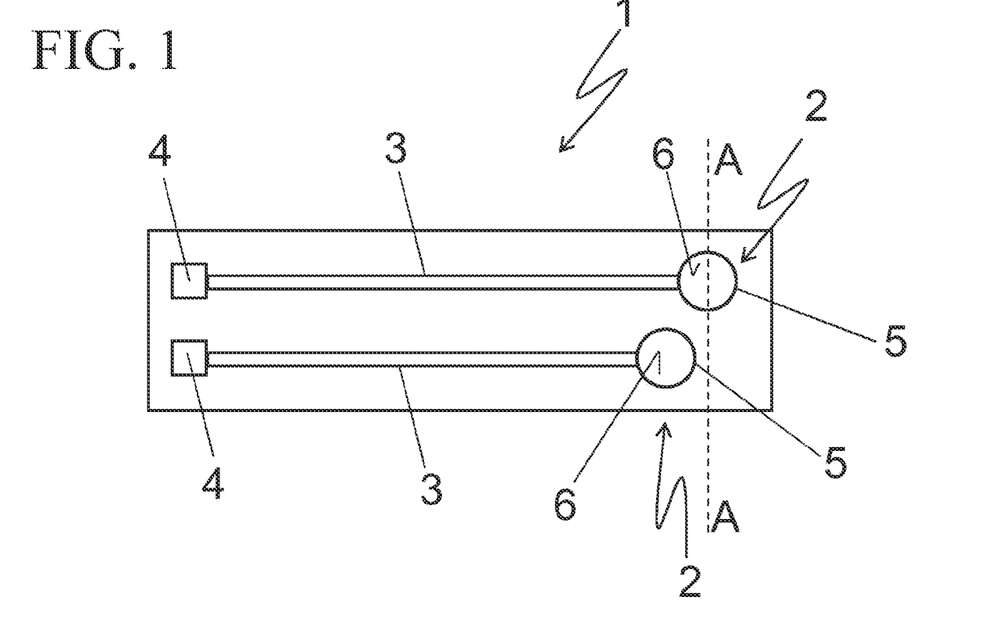
FIG. 1 depicts a schematic top view of an electrode device according to the present invention.

In FIG. 1 a top view onto an electrode device 1 is schematically depicted. According to FIG. 1 the electrode device 1 comprises two measurement electrodes 2, wherein each of the measurement electrodes 2 is connected via an electrically conducting trace 3 to a terminal 4.

In FIG. 1, for simplicity, the top layers of the electrode device 1 have been show transparent such that the metallization forming the measurement electrodes 5, the traces 3 and the terminals 4 is visible. Further, the number of measurement electrodes is limited to two. Each measurement electrode 2 consists of an electrically conducting pad 5 having a contact surface 6.

Figure 2A:
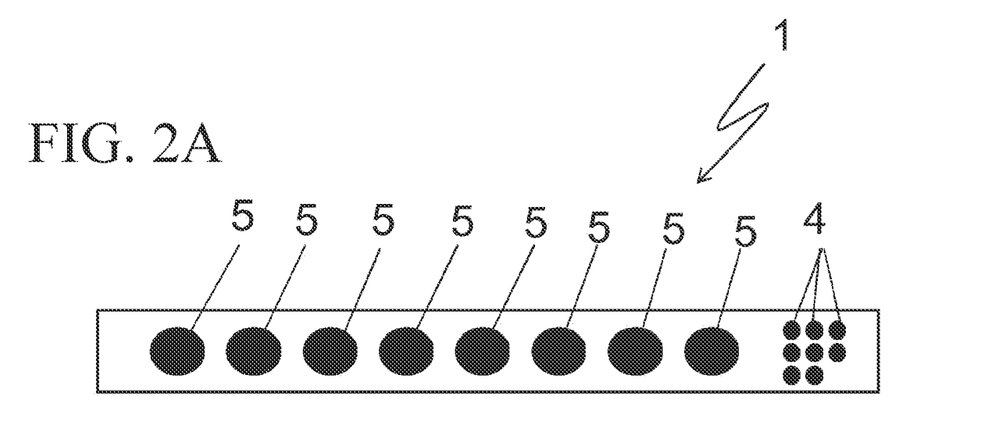

In contrast, the embodiment of FIG. 2 shows a plurality of measurement electrodes having electrically conducting pads 5, wherein in the top view of FIG. 2 *a*) only the exposed contact surfaces 6 of the measurement electrodes 5 are visible, while the traces are covered by the top layer of the electrode device 1. Further the terminals 4 electrically connected by the traces to the measurement electrodes 5 are visible as their contact surfaces are also exposed and not covered.

Figure 2B:
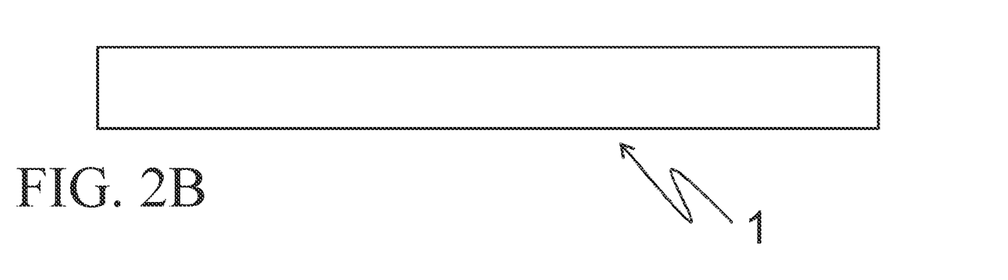

The measurement electrode device 1 is implantable, i.e. when in use it will be implanted in a patient. In the present embodiments, the implantable electrode device is thought to be implanted in a patient's head between the skin and the cranium. Thus the side of the electrode device 1 shown in FIGS. 1 and 2 *a*) when in use faces the patient's cranium, while the side of the device 1 shown in FIG. 2 *b*) faces away from the cranium.

The electrode device is part of an EEG system, wherein the terminals 4 of the electrode device 1 are electrically connected to an interface equipment (not shown) which forms an integral part of the implantable electrode device and serves in order to store and forward data collected by the measurement electrodes 2 to a data processor located outside the patient's head.

Returning to the embodiment of FIG. 1 the electrode device 1 has a length measured in a direction parallel to the traces 3 of 15 cm and a width of 2 cm (drawing not to scale).

Figure 3:
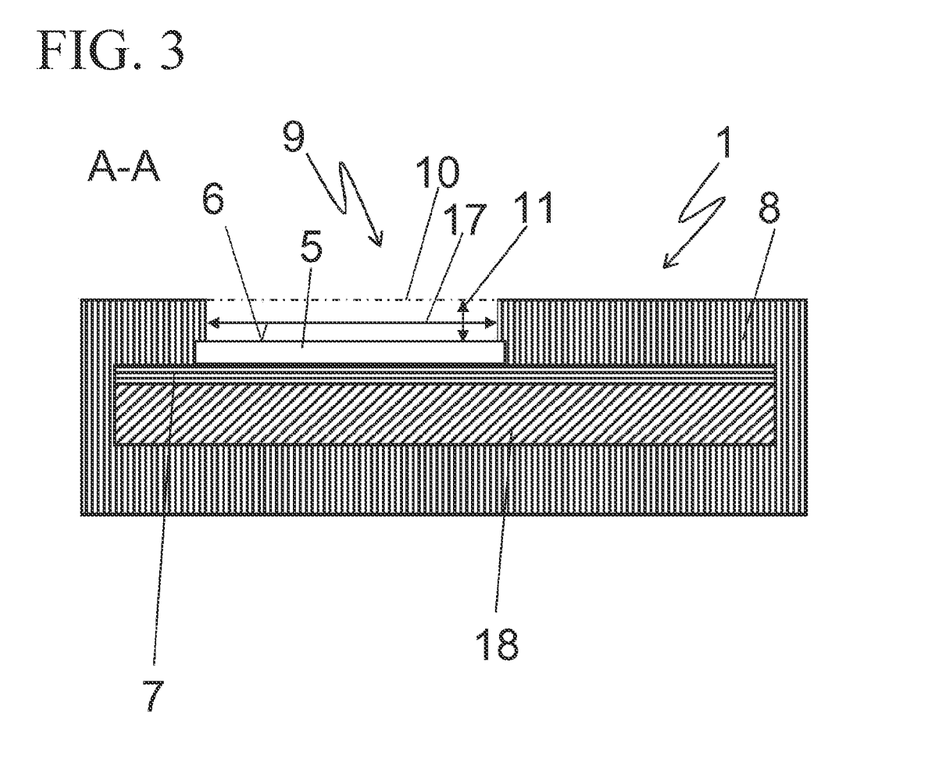
FIG. 3 shows a schematic cross-sectional view through an electrode device along line A-A of FIG. 1.

In order to provide a better understanding of the structural features of the electrode device 1 FIG. 3 shows a cross-sectional view along line A-A of FIG. 1. A core of the electrode device 1 which is also denoted a carrier 18 is made of a strip of PDMS having a thickness in a direction perpendicular to the contact surface 6 of 1,000 µm. PDMS has the advantage of providing a flexible electrically non conducting material, which in addition is approved for medical use even in implants.

On top of the carrier 18 a coating 7 of parylene is provided. This parylene coating 7 serves as an adhesion layer in order to provide a mechanically stable contact between the carrier 18 and the metallization 5. In addition, the coating 7 serves to mediate between the coefficient of thermal expansion of the carrier of PDMS and the metallization 5.

In the present examples, the metallization 5 of the measurement electrodes 2 consist of 200 nanometres platinum and the thermal coefficient of expansion of the parylene is between the thermal coefficient of expansion of PDMS and platinum.

The entire structure consisting of the carrier 18, the coating 7 as well as the metallization 5 is encapsulated by a further parylene layer 8.

The parylene layer 8 serves as the barrier layer in the sense of the present application. It forms a moisture barrier in order to prevent moisture from entering into the structure and leading to a peeling off or separation of the different parts or layers of the implantable electrode device 1. The barrier layer 8 has a thickness of 10 µm on each side of the electrode device 1. The barrier layer 8 is only removed above the contact surface 6 of the metallization 5 such that the contact surface 6 of the metallization forming the measurement electrode 5 is exposed to the outside environment without any dielectric placed on top. This way the contact surface 6 of the measurement electrode 5 can be put into direct contact with the patient's tissue and measure for example a brain's electrical discharges.

Not shown in FIG. 3 are silane undercoatings provided between the coating 7 of silane 7 and the carrier 18, between the barrier layer 8 and the coating 7 and between the barrier layer 8 and the carrier 18. These undercoating of silane provides an adhesion layer between parylene and PDMS, but also between two layers of parylene.

The schematic view of FIG. 3 also very clearly shows the requirements regarding the surface of the implantable electrode device 1. In order to reduce forces applied to the electrode device 1 by any tissue formed as an encapsulation growth along the surfaces of the electrode device 1, when removing the device from a patient, its surface on a side 9 thereof, on which the conducting pads 5 of the measurement electrodes 5 are located alternatively fulfills one of the following requirements:

As depicted in FIG. 3 one alternative is to limit the maximum valley depth 11 or a maximum peak height between the contact surface 6 and a meanline 10 of the surface of the electrode device 1 such that it is equal to or smaller than 60 µm.

In embodiments, wherein the metallization of the conducting pads of the measurement electrodes projects above the barrier layer 8 this would translate into a maximum peak height between a contact surface 6 and the meanline surface of the barrier layer 8 being equal to or smaller than 60 µm.

The meanline 10 of the surface of the electrode device is a straight line intersecting the actual profile of the surface the electrode device 1 such that the sum of all deviations of the meanline from the actual profile is minimized. It is evident that the meanline in this case is calculated excluding the surface of the measurement electrodes, i.e. the contact surface 6. The maximum valley depth in FIG. 3 is denoted by reference number 11.

Alternatively, once the maximum valley depth between the contact surface 6 of the measurement electrode 1 and the meanline 10 of the surface of the electrode device excluding the at least one measurement electrode is larger than 60 µm simultaneously the maximum linear extension of the contact surface 6 must be equal to or less than 100 µm. When viewed at FIG. 3, the linear extension of the contact surface is the diameter of the circular contact surface 6. The maximum linear extension of the contact surface 6 in FIG. 3 is denoted by reference number 17.

FIGS. 4 *a*) to *h*) schematically show a manufacturing process for providing a further embodiment of an electrode device 1 according to the present invention.

In FIG. 4 *a*), the initial manufacturing of the PDMS carrier 18 on a PMMA substrate 12 is shown. In order to obtain the carrier 18 of PDMS with the required thickness, PDMS at a ratio of 10:1 between the polymeric base and the curing agent is poured onto the PMMA acrylic substrate 12, wherein care must be taken that the PDMS mixture is fully degased before application thereof such that no bubbles are present in the mixture.

Figure 4A:
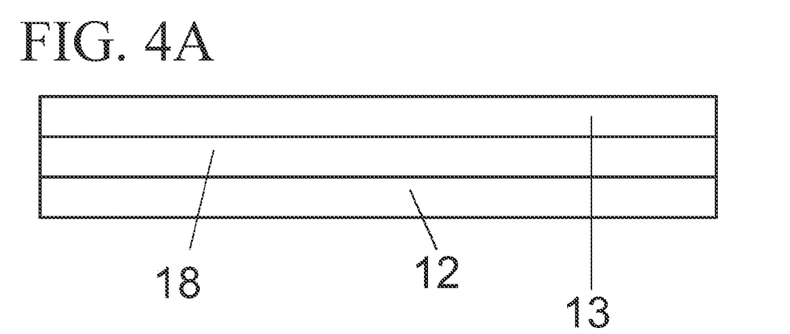

At the corners of the substrate spacers are placed, which hold a second substrate 13 of PMMA in a defined distance from the first substrate 12 and the liquid PDMS mixture is distributed between the two substrates such that its film thickness corresponds to the distance between the first and second substrates.

Figure 4B:
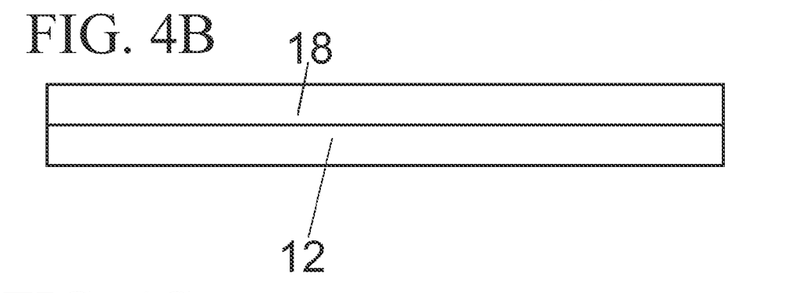

In the next step, the PDMS is cured for four hours at 60° C. forming a solid, but flexible substrate. In the present example, the thickness of the carrier 18 of PDMS amounts to 1000 µm. As can be seen in FIG. 4 *b*), the second substrate 13 afterwards is removed.

In order to make the PDMS adhere to a parylene layer to be applied, a mixture of silane solution with a ratio of IPA:DI water:A-174 silane of 100:100:1 is provided. The oven is preheated to 70° C. and the structure as depicted in FIG. 3*b* is rinsed in the silane solution for 30 minutes. Then the structure is removed and placed on lint free wipes for air drying. Then the structure is again rinsed with IPA for 15 seconds and air-dried again. In the last step, the structure is baked to completely dry in the oven.

FIG. 4 *c*) shows the structure not only after the silane undercoating 14 has been applied to the structure consisting of the PDMS film 6 and the substrate 12, but also the first parylene coating surface 15 with a thickness of 7 µm has been deposited by chemical vapor deposition on the silane undercoating 14.

Figure 4C:
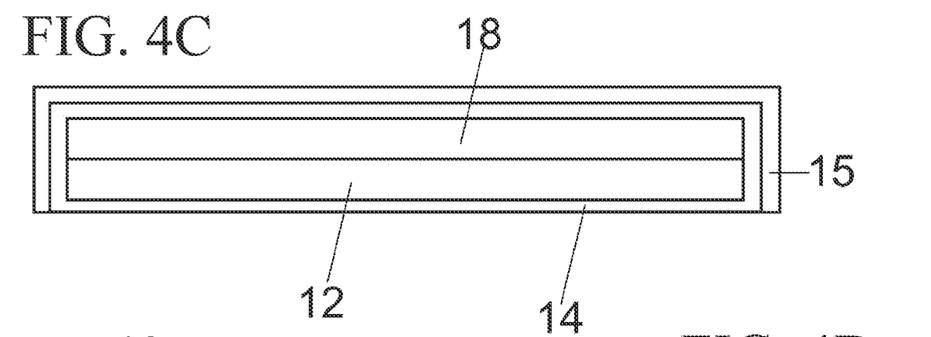
Figure 4D:
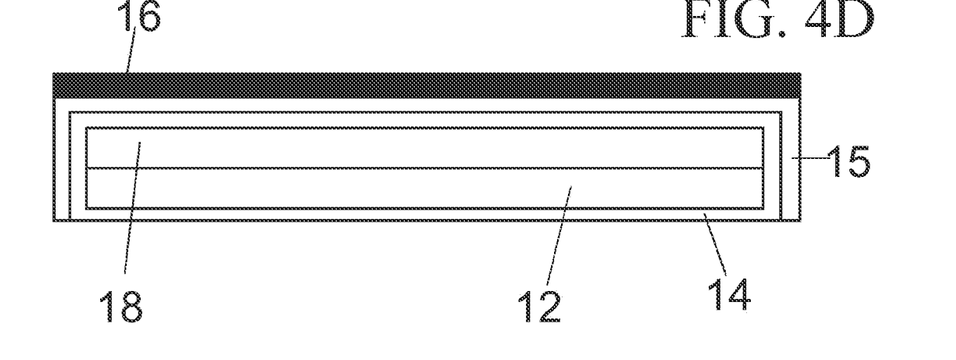

The coating 15 of parylene serves as a first moisture barrier as well as matching layer in order to match the coefficient of thermal expansion of the PDMS carrier 18 to the coefficient of thermal expansion of a metallization applied to the parylene coating 15. In this embodiment the parylene coating covers not only the top surface of the PDMS-carrier but also its side surfaces. Further the parylene coating 15 forms a contact layer enhancing the mechanical contact of a metallization to the underlying structure.

In the next step whose result is depicted in FIG. 4 *d*), 200 nm of platinum 16 are deposited on the parylene coating 15 by electron beam deposition.

Figure 4E:
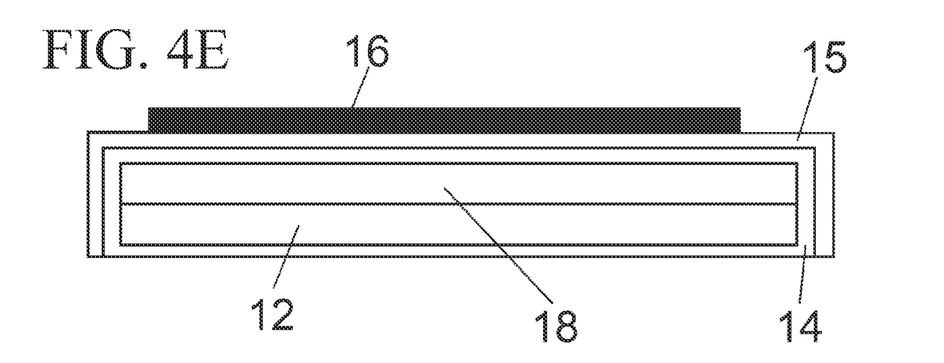
Figure 4F:
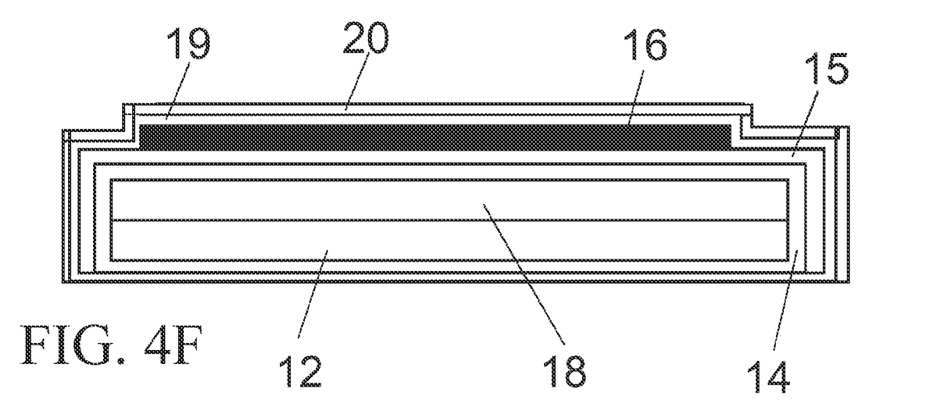

Then the platinum metallization 16 is then structured by laser ablating bits of the platinum film 16 such that only those parts of the metallization remain on the structure, which shall form the electrically conducting parts of the electrode device, in particular the conducting pad of the measurement electrode. Alternatively, the platinum can at minimum be structure such that at least the separate conducting pads of the measurement electrodes as well as the associated terminals and traces are electrically isolated from each other. The result of this structuring of the metallization is depicted in FIG. 4 e).

The results of a further application of a silane undercoating 19 and a subsequent processing of a parylene coating 20 is shown in FIG. 4 f), wherein the parylene coating 20 has a thickness of 10 μm.

Figure 4G:
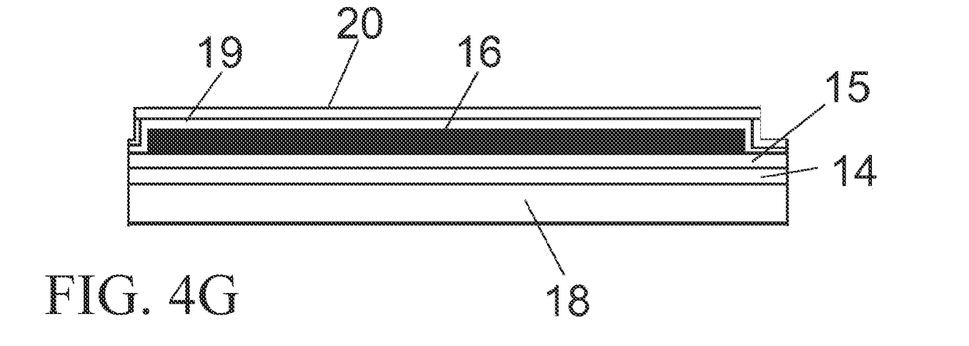
Figure 4H:
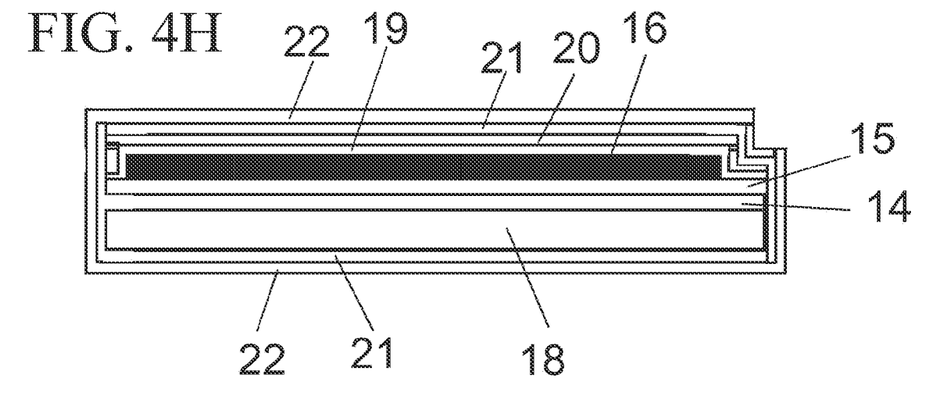

Then the entire structure is laser-cut in order to separate individual electrode devices formed on a single substrate 12. Furthermore, the PDMS carrier is peeled off from the lower PMMA substrate 12. The resulting structure is shown in FIG. 4 g).

Then another coating of silane 21 and parylene 22 is applied, which encapsulates the entire pre-fabricated structure as depicted in FIG. 4 h), i.e. this layer also covers the bottom side of the PDMS carrier 18, which previously had been in contact with the PMMA substrate 12. This final layer of parylene 22 is denoted the barrier layer.

Figure 4I:
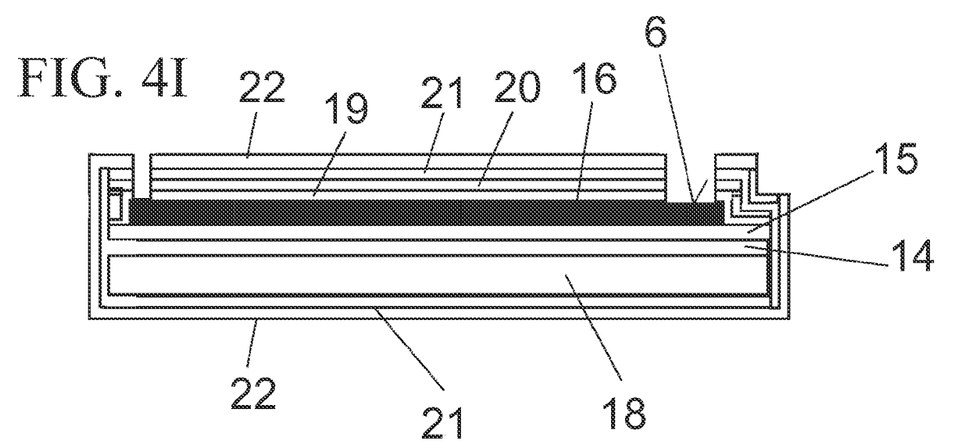

Finally, those bits of the metallization, which later shall form the contact surface of the electrically conducting pads of the measurement electrode and/or form the terminals for contacting of the electrode device, are burned free from any parylene and silane coating in order to expose the metal to the outside environment. The resulting electrode device is depicted in FIG. 4 i).

In the figures, identical elements have been denoted by identical reference numbers, even in distinct embodiments. The drawings are schematics only and not to scale.

The invention claimed is:

1. An implantable electrode device comprising:
a carrier made of a polymer material, wherein the carrier is flexible and electrically isolating;
at least one measurement electrode formed by an electrically conducting pad located on the carrier, wherein the electrically conducting pad has a contact surface;
a barrier layer enclosing the carrier by covering all surfaces of the carrier, wherein the contact surface of the electrically conducting pad is exposed to an outside environment;
at least one electrically conducting trace; and
at least one electrically conducting terminal;
wherein the electrically conducting trace electrically connects the measurement electrode to the electrically conducting terminal; and
wherein a material below an electrically conducting material, which forms the measurement electrode and forms at least one element selected from a group consisting of the electrically conducting trace and the electrically conducting terminal, has a thickness $d_{below}$, and a thickness of a material above the electrically conducting material has a thickness $d_{above}$, wherein the material above the electrically conducting material is a layered material comprising at least two layers, a first of the two layers having a first Young's modulus and a second of the two layers having a second Young's modulus different than the first Young's modulus, the thicknesses $d_{below}$ and $d_{above}$ fulfilling a relation $Y_{below}d_{below}=Y_{above}d_{above}$ wherein $Y_{below}$ is a Young's modulus of the material below the electrically conducting material and $Y_{above}$ is the Young's modulus of the material above the electrically conducting material.

2. The implantable electrode device of claim 1, wherein the surface of the implantable electrode device on the side on which the measurement electrode is located has the maximum valley depth or the maximum peak height between the contact surface of the measurement electrode and the meanline of the surface of the implantable electrode device being equal to or smaller than 50 micrometres.

3. The implantable electrode device of claim 1, wherein the surface of the implantable electrode device on the side on which the measurement electrode is located has the maximum valley depth or the maximum peak height between the contact surface of the measurement electrode and the meanline of the surface of the implantable electrode device being equal to or smaller than 30 micrometres.

4. The implantable electrode device of claim 3, wherein the surface of the implantable electrode device on the side on which the measurement electrode is located has the maximum valley depth or the maximum peak height between the contact surface of the measurement electrode and the meanline of the surface of the implantable electrode device being equal to or larger than 5 micrometres.

5. The implantable electrode device of claim 3, wherein the surface of the implantable electrode device on the side on which the measurement electrode is located has the maximum valley depth or the maximum peak height between the contact surface of the measurement electrode and the meanline of the surface of the implantable electrode device being equal to or larger than 10 micrometres.

6. The implantable electrode device of claim 3, wherein the surface of the implantable electrode device on the side on which the measurement electrode is located has the maximum valley depth or the maximum peak height between the contact surface of the measurement electrode and the meanline of the surface of the implantable electrode device being equal to or larger than 12 micrometres.

7. The implantable electrode device of claim 1, wherein the barrier layer is electrically isolating and impermeable for liquids.

8. The implantable electrode device of claim 1, wherein the barrier layer is made of parylene.

9. The implantable electrode device of claim 1, wherein the barrier layer covers a front side, a back side and the side faces of the carrier.

10. The implantable electrode device of claim 1, wherein the carrier is made of a silicon-based organic polymer, preferably of polydimethylsiloxane.

11. The implantable electrode device of claim 1, wherein the measurement electrode is formed on a coating on the carrier.

12. The implantable electrode device of claim 1, wherein the barrier layer is formed on a coating on the carrier.

13. The implantable electrode device of claim 1, wherein the implantable electrode device has a thickness in a range from 800 micrometres to 1,500 micrometres.

14. The implantable electrode device of claim 1, further comprising an interface equipment electrically coupled to the electrically conducting terminal.

15. An implantable electrode device comprising:
a carrier made of a polymer material, wherein the carrier is flexible and electrically isolating;
at least one measurement electrode formed by an electrically conducting pad located on the carrier, wherein the electrically conducting pad has a contact surface;

a barrier layer enclosing the carrier by covering all surfaces of the carrier, wherein the contact surface of the electrically conducting pad is exposed to an outside environment;
at least one electrically conducting trace; and
at least one electrically conducting terminal;
wherein the electrically conducting trace electrically connects the measurement electrode to the electrically conducting terminal; and
wherein a material below an electrically conducting material, which forms the measurement electrode and forms at least one element selected from a group consisting of the electrically conducting trace and the electrically conducting terminal, has a thickness $d_{below}$, and a thickness of a material above the electrically conducting material has a thickness $d_{above}$, wherein the material above the electrically conducting material is a layered material comprising at least two layers, a first of the two layers having a first Young's modulus and a second of the two layers having a second Young's modulus different than the first Young's modulus, the thicknesses $d_{below}$ and $d_{above}$ fulfilling a relation $Y_{below}d_{below}=Y_{above}d_{above}$ wherein $Y_{below}$ is a Young's modulus of the material below the electrically conducting material and $Y_{above}$ is the Young's modulus of the material above the electrically conducting material.

16. A system comprising:
a data processor; and
an implantable electrode device, wherein the implantable electrode device comprises:
 a carrier made of a polymer material, wherein the carrier is flexible and electrically isolating;
 at least one measurement electrode formed by an electrically conducting pad located on the carrier, wherein the electrically conducting pad has a contact surface;
 a barrier layer enclosing the carrier by covering all surfaces of the carrier, wherein the contact surface of the electrically conducting pad is exposed to an outside environment;
 at least one electrically conducting trace; and
 at least one electrically conducting terminal;
 wherein the electrically conducting trace electrically connects the measurement electrode to the electrically conducting terminal; and
 wherein a material below an electrically conducting material, which forms the measurement electrode and forms at least one element selected from a group consisting of the electrically conducting trace and the electrically conducting terminal, has a thickness $d_{below}$, and a thickness of a material above the electrically conducting material has a thickness $d_{above}$, wherein the material above the electrically conducting material is a layered material comprising at least two layers, a first of the two layers having a first Young's modulus and a second of the two layers having a second Young's modulus different than the first Young's modulus, the thicknesses $d_{below}$ and $d_{above}$ fulfilling a relation $Y_{below}d_{below}=Y_{above}d_{above}$ wherein $Y_{below}$ is a Young's modulus of the material below the electrically conducting material and $Y_{above}$ is the Young's modulus of the material above the electrically conducting material;
wherein the data processor comprises a first interface equipment in communication with a second interface equipment of the implantable electrode device when in use.

17. A system comprising:
a data processor; and
an implantable electrode device, wherein the implantable electrode device comprises:
 a carrier made of a polymer material, wherein the carrier is flexible and electrically isolating;
 at least one measurement electrode formed by an electrically conducting pad located on the carrier, wherein the electrically conducting pad has a contact surface;
 a barrier layer enclosing the carrier by covering all surfaces of the carrier, wherein the contact surface of the electrically conducting pad is exposed to an outside environment;
 at least one electrically conducting trace; and
 at least one electrically conducting terminal;
 wherein the electrically conducting trace electrically connects the measurement electrode to the electrically conducting terminal; and
 wherein a material below an electrically conducting material, which forms the measurement electrode and forms at least one element selected from a group consisting of the electrically conducting trace and the electrically conducting terminal, has a thickness $d_{below}$, and a thickness of a material above the electrically conducting material has a thickness $d_{above}$, wherein the material above the electrically conducting material is a layered material comprising at least two layers, a first of the two layers having a first Young's modulus and a second of the two layers having a second Young's modulus different than the first Young's modulus, the thicknesses $d_{below}$ and $d_{above}$ fulfilling a relation $Y_{below}d_{below}=Y_{above}d_{above}$ wherein $Y_{below}$ is a Young's modulus of the material below the electrically conducting material and $Y_{above}$ is the Young's modulus of the material above the electrically conducting material;
wherein the data processor comprises a first interface equipment in communication with a second interface equipment of the implantable electrode device when in use.

18. A method for manufacturing an implantable electrode device comprising:
 providing a substrate;
 applying a liquid polymer material onto the substrate;
 confining the liquid polymer material to define a desired height;
 curing the liquid polymer material to form a solid, flexible and electrically isolating polymer material providing a carrier;
 depositing an electrically conducting material on the carrier;
 structuring of the electrically conducting material in order to define at least one measurement electrode formed by an electrically conducting pad having a contact surface, at least one electrically conducting trace, and at least one electrically conducting terminal, wherein the electrically conducting trace electrically connects the measurement electrode and the terminal;
 removing the substrate; and
 coating of a barrier layer onto the structure comprising the carrier and the electrically conducting material so that the barrier layer encloses the structure by covering all surfaces of the structure;
 wherein a material below an electrically conducting material, which forms the measurement electrode and forms at least one element selected from a group consisting of the electrically conducting trace and the electrically conducting terminal, has a thickness $d_{below}$, and a thickness of a material above the electrically conducting material has a thickness $d_{above}$, wherein the material above the electrically conducting material is a layered material comprising at least two layers, a first of the two layers having a first Young's modulus and a second of the two layers having a second Young's modulus different than the first Young's modulus, the thicknesses $d_{below}$ and $d_{above}$ fulfilling a relation $Y_{below}d_{below}=Y_{above}d_{above}$ wherein $Y_{below}$ is a Young's modulus of the material below the electrically conducting material and $Y_{above}$ is the Young's modulus of the material above the electrically conducting material.

19. The method of claim 18, wherein the implantable electrode device is configured to be implanted into a human or animal body and configured to be inserted under between two skin layers of the human or animal body.

* * * * *